United States Patent [19]
Cauwet et al.

[11] Patent Number: 5,900,232
[45] Date of Patent: * May 4, 1999

[54] COSMETIC COMPOSITIONS CONTAINING AT LEAST ONE ANIONIC SURFACTANT OF ALKYLGALACTOSIDE URONATE TYPE AND AT LEAST ONE CATIONIC POLYMER, AND USES THEREOF IN THE TREATMENT OF KERATINOUS SUBSTANCES

[75] Inventors: Daniele Cauwet, Paris; Claude Dubief, Le Chesnay, both of France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/553,428
[22] PCT Filed: Jun. 1, 1994
[86] PCT No.: PCT/FR94/00642
§ 371 Date: Nov. 28, 1995
§ 102(e) Date: Nov. 28, 1995
[87] PCT Pub. No.: WO94/27575
PCT Pub. Date: Dec. 8, 1994

[30] Foreign Application Priority Data

Jun. 1, 1993 [FR] France ................................. 9306531

[51] Int. Cl.[6] .............................. A61K 7/48; A61K 7/00
[52] U.S. Cl. ................................ 424/70.22; 424/70.13; 424/70.17; 514/846; 514/847
[58] Field of Search ........................ 424/70.11, 70.22, 424/70.19, 70.13, 70.17; 514/846, 847

[56] References Cited

U.S. PATENT DOCUMENTS 3,980,769 9/1976 Ghilardi et al. ........................ 424/70

FOREIGN PATENT DOCUMENTS

| 0 275 153 | 7/1988 | European Pat. Off. . |
| 0 337 354 | 10/1989 | European Pat. Off. . |
| 0 532 370 | 7/1993 | European Pat. Off. . |
| 0 550 276 | 7/1993 | European Pat. Off. . |
| 2 197 567 | 3/1974 | France . |
| WO92/10162 | 6/1992 | WIPO . |
| WO93/02092 | 2/1993 | WIPO . |

Primary Examiner—Sally Gardner-Lane
Attorney, Agent, or Firm—Jacobson, Price, Holman & Stern, PLLC

[57] ABSTRACT

Cosmetic compositions containing in an aqueous medium an alkylgalactoside uronate and a cationic polymer and their use in the treatment or washing of keratinous materials. The alkylgalactoside uronate is based on formula (I):

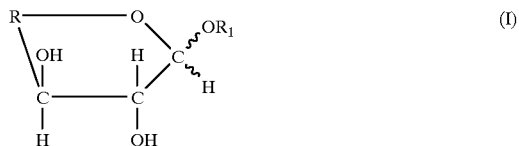

$R_1$ is a $C_8$–$C_{22}$ alkyl;
R is (i) CH—CH(OH)—$CO_2R_2$ or (ii) —CH(OH)—CH—$CO_2R_2$,
with the carbon carrying the hydroxyl group being linked to the endocyclic oxygen atom;
$R_2$ is hydrogen, an alkaline metal, an alkaline-earth metal or a quaternary ammonium group.

17 Claims, No Drawings

COSMETIC COMPOSITIONS CONTAINING AT LEAST ONE ANIONIC SURFACTANT OF ALKYLGALACTOSIDE URONATE TYPE AND AT LEAST ONE CATIONIC POLYMER, AND USES THEREOF IN THE TREATMENT OF KERATINOUS SUBSTANCES

This applications claims priority under 35 USC 371 to PCT/FR 94/00642 filed Jun. 1, 1994.

The invention relates to cosmetic compositions containing at least one anionic surfactant of alkylgalactoside uronate type and at least one cationic polymer and to the use thereof in the treatment and washing of keratinous substances.

Compositions for washing the hair or the skin are generally formulated from anionic or nonionic surfactants or their mixtures, optionally in the presence of amphoteric surfactants.

Hair attacked by atmospheric agents such as light or chemical treatments and washed with conventional washing compositions is difficult to disentangle and this disadvantage is found to be further accentuated in the case of wet hair.

It has been proposed to add cationic polymers to such washing bases in order to improve the disentangling properties but the volume and the amount of the lathers, in particular their softness and their compactness, are not satisfactory.

Anionic surfactants of alkylgalactoside uronate type have already been recommended in washing compositions for the hair. They have been described in Patent Application EP-A-0,532,370.

Compositions for washing the hair which use these anionic or nonionic surfactants alone do not lead to good cosmetic properties; in particular, the disentangling of wet hair is difficult.

The Applicant Company has just surprisingly discovered that the combination, in washing and/or treating compositions for keratinous substances, of an anionic surfactant of alkylgalactoside uronate type and of a cationic polymer confer greatly improved disentangling properties, in particular for wet hair, on these compositions.

Moreover, the combination in accordance with the present invention makes it possible to obtain a copious, compact and very soft lather.

In addition, the Applicant Company has observed that the cosmetic compositions containing such a combination confer good cosmetic properties, such as softness and a pleasant feel, on keratinous substances.

The subject of the present invention is therefore cosmetic compositions containing at least one anionic surfactant of alkylgalactoside uronate type and at least one cationic polymer, with the exception of cationic cellulose ethers.

Another subject of the invention consists of the use of these compositions for treating and/or washing keratinous substances such as the hair or the skin.

Another subject relates to cosmetic treatment processes for the hair or for the skin by means of the compositions of the invention; washing and treatment processes for the hair being preferred.

The cosmetic compositions according to the invention contain, in a cosmetically acceptable aqueous medium, at least one alkylgalactoside uronate and at least one cationic polymer, with the exception of cationic celluloses such as cationic cellulose ethers or quaternized celluloses.

The alkylgalactoside uronates which can be used in accordance with the invention correspond to the following formula (I):

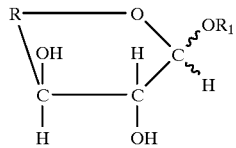

in which:

$R_1$ denotes a linear or branched alkyl radical containing 8 to 22 carbon atoms.

R denotes a group
 (i) >CH—CH(OH)—CO$_2$R or
 (ii) —CH(OH)—CH—CO$_2$R$_2$, in which the carbon carrying the hydroxyl group is connected to the endocyclic oxygen atom; $R_2$ being hydrogen, an alkali metal, an alkaline-earth metal or a quaternary ammonium group which is unsubstituted or substituted by alkyl or hydroxyalkyl radicals or derived from an amino acid.

The anionic surfactants of alkylgalactoside uronate type of formula (I) are known and can be prepared according to the processes described in Patent Application EP-A-0,532,370.

The alkali metal is in particular sodium or potassium and the alkaline-earth metal is preferably magnesium. Mention may be made, as quaternary ammonium salts, of the salts of ammonia, of triethanolamine, of monoethanolamine, of 2-amino-2-methyl-1,3-propanediol or of 2-amino-2-methyl-1-propanol; the amino acid is in particular histidine, arginine or lysine.

Use is preferably made of the compounds of formula (I) in which the $R_1$ radical denotes a $C_8$–$C_{14}$ alkyl and more particularly the decyl radical.

Use is in particular made of the following compounds:

Sodium decylα-D-galactopyranoside uronate:

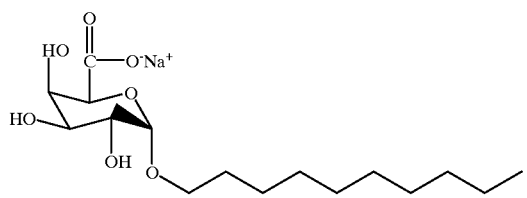

Sodium decylβ-D-galactopyranoside uronate:

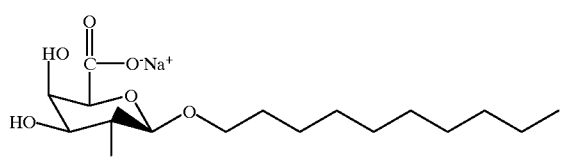

Sodium decylα-D-galactofuranoside uronate:

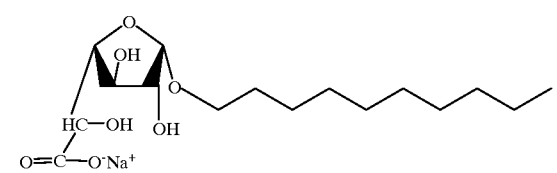

Sodium decyl β-D-galactofuranoside uronate:

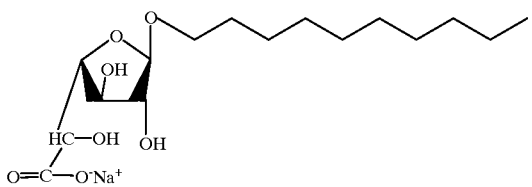

The cationic polymers which can be used in accordance with the invention are chosen from polymers, containing primary, secondary, tertiary and/or quaternary amine groups which form part of the polymer chain or are directly connected to the latter, which have a molecular weight of between 500 and approximately 5,000,000 and preferably between 1000 and 3,000,000, with the exception of cationic celluloses such as cationic cellulose ethers or quaternized celluloses.

Among these polymers, there may be mentioned more particularly the quaternized proteins and the polymers of the polyamine or polyaminoamide type or of the quaternary polyammonium type in which the ammonium group forms part of a ring or of the polymer chain or is attached to the polymer chain by a hydrocarbon radical.

The quaternized proteins are in particular polypeptides which are chemically modified and which carry quaternary ammonium groups at the chain end or grafted on the latter. Mention may in particular be made, among these proteins, of:

collagen hydrolysates carrying triethylammonium groups such as the products sold under the name "Quat-Pro E" by the company Maybrook and called, in the CTFA dictionary, "Triethonium Hydrolyzed Collagen Ethosulfate";

collagen hydrolysates carrying trimethylammonium or dimethylstearylammonium chloride groups such as the products sold under the name of "Quat-Pro S" by the company Maybrook and called, in the CTFA dictionary, "Steartrimonium Hydrolyzed Collagen";

animal protein hydrolysates carrying dimethylbenzylammonium groups such as the products sold under the name "Crotein BTA" by the company Croda and called, in the CTFA dictionary, "Benzyltrimonium Hydrolyzed Animal Protein";

protein hydrolysates carrying, on the polypeptide chain, quaternary ammonium groups containing at least one alkyl radical having from 1 to 18 carbon atoms. Among these protein hydrolysates, there may be mentioned among others:

Croquat L, in which the polypeptide chain has an average molecular weight of approximately 2,500 and in which the quaternary ammonium group contains a $C_{12}$ alkyl group;

Croquat M, in which the polypeptide chain has an average molecular weight of approximately 2,500 and in which the quaternary ammonium group contains a $C_{10}$–$C_{18}$ alkyl group;

Croquat S, in which the polypeptide chain has an average molecular weight of approximately 2,700 and in which the quaternary ammonium group contains a $C_{18}$ alkyl group;

Crotein Q, in which the polypeptide chain has an average molecular weight of the order of 12,000 and in which the quaternary ammonium group contains at least one alkyl group having from 1 to 18 carbon atoms;

quaternized vegetable proteins such as the quaternized vegetable protein from soya sold under the name Croquat Soya.

These various products are sold by the Company Croda.

Other quaternized proteins are those corresponding to the formula:

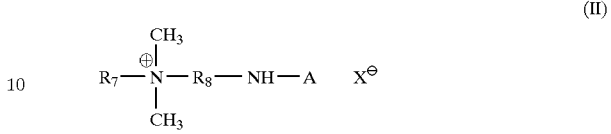

(II)

in which A denotes a protein residue derived from collagen protein hydrolysates, $R_7$ denotes a lipophilic group containing up to 30 carbon atoms, $R_8$ represents an alkylene group having 1 to 6 carbon atoms, $X^{\ominus}$ represents an anion derived from an organic or inorganic acid; the proteins have a molecular weight of between 1500 and 10,000, preferably 2000 and 5000. The preferred products are those sold under the name "Lexein QX 3000" by the Company Inolex, called, in the CTFA dictionary, "Cocotrimonium Collagen Hydrolysate".

The polymers of the polyamine, polyaminoamide or quaternary polyammonium type which can be used in accordance with the present invention are described in particular in the French patents of the Applicant Company No. 2,505,348 or 2,542,997.

Among these polymers, there may be mentioned:

(1) optionally quaternized vinylpyrrolidone/ dialkylaminoalkyl acrylate or methacrylate copolymers, such as the products sold under the name "Gafquat" by the Company Gaf Corporation, such as, for example, "Gafguat 734 or 755", or else the products called "Copolymer 845, 958 and 937". These polymers are described in detail in French Patents 2,077,143 and 2,393,573.

(2) The noncellulose cationic polysaccharides described more particularly in U.S. Pat. Nos. 3,589,578 and 4,031,307 and more particularly the product marketed under the name "Jaguar C. 13 S" sold by the Company Meyhall.

(3) Polymers consisting of piperazinyl units and of divalent, straight- or branched-chain alkylene or hydroxyalkylene radicals, optionally interrupted by oxygen, sulphur or nitrogen atoms or by aromatic or heterocyclic rings, as well as the oxidation and/or quaternization products of these polymers. Such polymers are described in French Patents 2,162,025 and 2,280,361.

(4) Water-soluble polyaminoamides prepared in particular by polycondensation of an acid compound with a polyamine. These polyaminoamides can be crosslinked by an epihalohydrin, a diepoxide, a dianhydride, an unsaturated anhydride, a bisunsaturated derivative, a bishalohydrin, a bisazetidinium, a bishaloacyldiamine, an alkyl bishalide or alternatively by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the cross-linking agent being used in proportions ranging from 0.025 to 0.35 mol per amine group of the polyaminoamide.

These polyaminopolyamides can be alkylated or, if they contain one or more tertiary amine functional groups, quaternized. Such polymers are described in particular in French Patents 2,252,840 and 2,368,508.

(5) Polyaminoamide derivatives resulting from the condensation of polyalkylenepolyamines with polycarboxylic acids followed by an alkylation by bifunctional agents.

There may be mentioned, for example, the adipic acid/dialkylaminohydroxyalkyldialkylenetriamine polymers in which the alkyl radical contains 1 to 4 carbon atoms and preferably denotes methyl, ethyl or propyl. Such polymers are described in French Patent 1,583,363.

Among these derivatives, there may be more particularly mentioned the adipic acid/dimethylaminohydroxypropyl/diethylenetriamine polymers sold under the name "Cartaretine F, $F_4$ or $F_8$" by the Company Sandoz.

(6) Polymers obtained by reaction of a polyalkylenepolyamine containing two primary amine groups and at least one secondary amine group with a dicarboxylic acid chosen from diglycolic acid and saturated aliphatic dicarboxylic acids having from 3 to 8 carbon atoms. The molar ratio of polyalkylenepolyamine to dicarboxylic acid being between 0.8:1 and 1.4:1; the polyaminoamide resulting therefrom being brought to react with epichlorohydrin in a molar ratio of epichlorohydrin in relation to the secondary amine group of the polyaminoamide of between 0.5:1 and 1.8:1. Such polymers are described in particular in U.S. Pat. Nos. 3,227,615 and 2,961,347.

Polymers of this type are in particular marketed under the name "Hercosett 57" by the Company Hercules Incorporated or else under the name of "PD 170" or "Delsette 101" by the Company Hercules in the case of the adipic acid/epoxypropyl/diethylenetriamine copolymer.

(7) Cyclopolymers having a molecular weight of 20,000 to 3,000,000 such as the homopolymers containing, as principal constituent of the chain, units corresponding to the formulae (III) or (III').

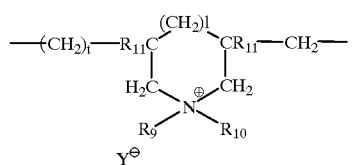
(III)

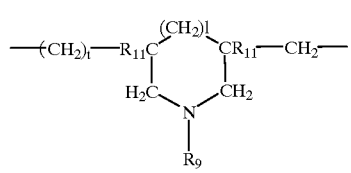
(III')

1 and t are equal to 0 or 1, and the sum 1+t=1; $R_{11}$ denotes hydrogen or methyl, $R_9$ and $R_{10}$ denote, independently of each other, an alkyl group having from 1 to 22 carbon atoms, a hydroxyalkyl group in which the alkyl group preferably has 1 to 5 carbon atoms or a lower amidoalkyl group or $R_9$ and $R_{10}$ can form, jointly with the nitrogen atom to which they are connected, heterocyclic groups such as piperidinyl or morpholinyl, as well as copolymers containing units of formula (III) or (III') and units derived from acrylamide or from diacetone acrylamide, $Y^{\ominus}$ is an anion such as bromide, chloride, acetate, borate, citrate, tartrate, bisulfate, bisulfite, sulfate or phosphate. Among the polymers defined above, there may be more particularly mentioned the homopolymer of dimethyldiallylammonium chloride sold under the name "Merquat 100", which has a molecular weight of less than 100,000, and the copolymer of dimethyldiallylammonium chloride and of acrylamide which has a molecular weight of greater than 500,000 and is sold under the name of "Merquat 550" and "Merquat S" by the Company Merck.

These polymers are described more particularly in French Patent 2,080,759 and its Certificate of Addition No. 2,190,406.

(8) Homopolymers or copolymers derived from acrylic or methacrylic esters or amides and containing the units:

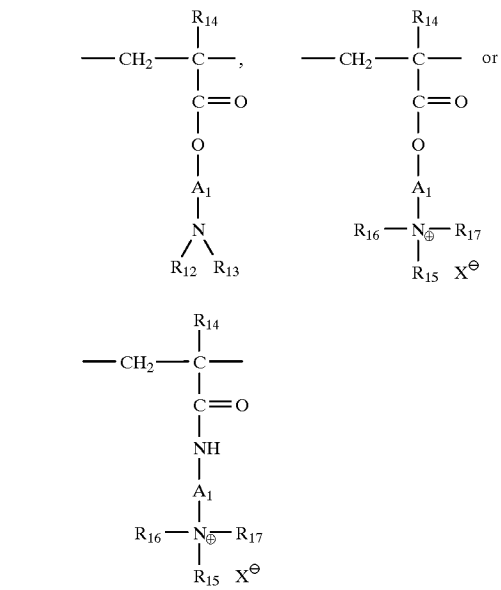

in which $R_{14}$ denotes a hydrogen atom or a methyl radical, $A_1$ is a linear or branched alkylene group of 1 to 6 carbon atoms or a hydroxyalkylene group of 1 to 4 carbon atoms;

$R_{15}$, $R_{16}$ and $R_{17}$, which are identical or different, represent an alkyl group having from 1 to 18 carbon atoms or a benzyl radical, $R_{12}$ and $R_{13}$ represent a hydrogen atom or an alkyl group having from 1 to 6 carbon atoms, $X^{\ominus}$ denotes a methosulfate anion or a halide such as chloride or bromide.

The comonomer(s) which may be used belong(s) to the family of the: acrylamide, methacrylamide, diacetone acrylamide, acrylamide and methacrylamide substituted at the nitrogen by lower alkyls, acrylic or methacrylic acid esters, vinylpyrrolidone, vinyl esters or vinylcaprolactam.

Among these compounds, there may be mentioned the copolymer of acrylamide and of dimethylaminoethyl methacrylate quaternized with dimethyl sulfate and sold under the name "Hercofloc" by the Company Hercules, the copolymer of acrylamide and of methacryloyloxyethyltrimethylammonium chloride described in Patent Application EP-A-80976 and sold under the name "Bina Qat P100" by the Company Ciba-Geigy, or alternatively the poly (methacrylamidopropyltrimethylammonium chloride) sold under the name "Polymaptac" by the Company Texaco Chemicals.

(9) Quaternary polymers of vinylpyrrolidone and of vinylimidazole such as, for example, the products marketed under the names "Luviquat FC 905, FC 550 and FC 370" by the Company B.A.S.F.

(10) Polyamines such as "Polyquart H" sold by the Company Henkel, referenced under the name of "Polyethylene Glycol (15) Tallow Polyamine" in the CTFA dictionary.

(11) The quaternary polyammonium polymers containing repeat units corresponding to the formula:

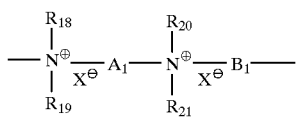

(IV)

in which $R_{18}$, $R_{19}$, $R_{20}$ and $R_{21}$, being identical or different, represent aliphatic, alicyclic or arylaliphatic radicals containing 1 to 20 carbon atoms or lower hydroxy alkylaliphatic radicals or else $R_{18}$, $R_{19}$, $R_{20}$ and $R_{21}$, together or separately, form, with the nitrogen atoms to which they are connected, heterocycles which optionally contain a second heteroatom other than nitrogen or else $R_{18}$, $R_{19}$, $R_{20}$ and $R_{21}$ represent a linear or branched $C_1$–$C_6$ alkyl radical substituted with a nitrile, ester, acyl, amide or $$-\overset{O}{\underset{\|}{C}}-O-R_{22}-D \quad \text{or} \quad -\overset{O}{\underset{\|}{C}}-NH-R_{22}-D$$

group, where $R_{22}$ is an alkylene and D a quaternary ammonium group.

$A_1$ and $B_1$ represent polymethylene groups containing from 2 to 20 carbon atoms which may be linear or branched, saturated or unsaturated, and which may contain, connected to or inserted into the principal chain, one or more aromatic rings or one or more oxygen or sulfur atoms or sulfoxide, sulfone, disulfide, amino, alkylamino, hydroxyl, quaternary ammonium, ureido, amide or ester groups, and $X^{\ominus}$ denotes an anion derived from an inorganic or organic acid.

$R_{18}$ and $R_{20}$ may form, with the two nitrogen atoms to which they are connected, a piperazine ring; additionally, if $A_1$ denotes a linear or branched, saturated or unsaturated alkylene or hydroxyalkylene radical, $B_1$ may also denote a group:

$-(CH_2)_n-CO-D-OC-(CH_2)_n-$ in which D denotes:
a) a glycol residue of formula: $-O-Z-O-$ where Z denotes a linear or branched hydrocarbon radical or a group corresponding to the formulae:

$$-\left[CH_2-CH_2-O\right]_x-CH_2-CH_2-$$

$$-\left[CH_2-\underset{CH_3}{\underset{|}{CH}}-O\right]_y-CH_2-\underset{CH_3}{\underset{|}{CH}}-$$

where x and y denote an integer from 1 to 4, representing a defined and single degree of polymerization or any number whatsoever from 1 to 4 representing an average degree of polymerization;
b) a bis-secondary diamine residue such as a piperazine derivative;
c) a bis-primary diamine residue of formula:

$-NH-Y-NH-$ where Y denotes a linear or branched hydrocarbon radical, or else the bivalent radical $-CH_2-CH_2-S-S-CH_2-CH_2-$ d) a ureylene group of formula:

$-NH-CO-NH-$;

$X^{\ominus}$ is an anion such as choride or bromide.

These polymers have a molecular mass generally of between 1,000 and 100,000.

Polymers of this type are described in particular in French Patents 2,320,330, 2,270,846, 2,316,271, 2,336,434 and 2,413,907 and Patents U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(12) Quaternary polyammonium polymers consisting of units of formula:
in which:

$R_{23}$, $R_{24}$, $R_{25}$ and $R_{26}$, which are identical or different, represent a hydrogen atom or a methyl, ethyl, propyl, β-hydroxyethyl, β-hydroxypropyl or $-CH_2CH_2(OCH_2CH_2)_pOH$ radical,

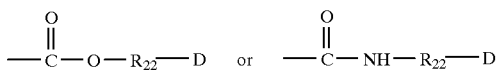

(V)

where p is equal to 0 or to an integer of between 1 and 6, with the proviso that $R_{23}$, $R_{24}$, $R_{25}$ and $R_{26}$ do not simultaneously represent a hydrogen atom;

x and y, which are identical or different, are integers of between 1 and 6;

m is equal to 0 or to an integer of between 1 and 34;

X denotes a halogen atom;

A denotes a dihalide radical and preferably represents $-CH_2-CH_2-O-CH_2-CH_2-$ Such compounds are described in more detail in Application EP-A-122,324.

It is possible, for example, to mention among the latter the products "Mirapol A 15", "Mirapol AD 1", "Mirapol AZ 1" and "Mirapol 175", sold by the Company Miranol.

Other cationic polymers which can be used in accordance with the invention are polyalkyleneimines, in particular polyethyleneimines, polymers containing vinylpyridine or vinylpyridinium units, condensates of polyamines and of epichlorohydrin, quaternary polyureylenes and chitin derivatives.

The alkylgalactoside uronates of formula (I) are present in the compositions in accordance with the invention in proportions of between 1 and 50% by weight with respect to the total weight of the composition.

The cationic polymers defined above are present in the compositions in accordance with the invention in proportions of between 0.01 and 10% by weight with respect to the total weight of the composition.

According to an embodiment of the invention, the composition contains at least one alkylgalactoside uronate of formula (I) as defined above and in which, when $R_2$ represents an alkali metal, the latter is other than sodium, and at least one cationic polymer as defined above.

According to another embodiment of the invention, the composition contains the combination of at least one sodium alkylgalactoside uronate and of at least one quaternized protein as defined above.

If the compositions according to the invention are not used for washing keratinous substances, the total concentration of anionic surfactants of formula (I) is between 1 and 10% and more particularly between 1 and 5% by weight with respect to the total weight of the composition. These compositions are used in particular as compositions to be rinsed or not to be rinsed, applied before or after shampooing, dyeing, bleaching, perming or hair straightening or in bleaching, dyeing, perming or hair-straightening compositions.

When the compositions according to the invention are washing compositions, they contain the surfactants of formula (I) in a total concentration of between 4 and 50% by weight and preferably between 8 and 40% by weight with respect to the total weight of the composition.

The compositions can contain, in addition to the anionic surfactants of formula (I), other surfactants of anionic, nonionic, amphoteric, zwitterionic or cationic nature.

Among the anionic surfactants, there may be mentioned the alkali metal salts, the ammonium salts, the amine salts, the aminoalcohol salts or the magnesium salts of the following compounds: the fatty acids, alkyl sulfates, alkyl ether sulfates, alkylamidoether sulfates, alkylarylpolyether sulfates or monoglyceride sulfates; the alkylsulfonates, alkylethersulfonates, alkylamidesulfonates, alkylarylsulfonates, olefinsulfonates or paraffinsulfonates; the alkylsulfosuccinates, the alkylethersulfosuccinates or the alkylamidesulfosuccinates; the alkylsulfosuccinamates; the alkylsulfoacetates; the alkyl ether phosphates; the acylsarcosinates, acylglutamates or N-acyltaurates; or the isethionates.

The alkyl or acyl radical of these various compounds generally consists of a carbon chain containing from 10 to 20 carbon atoms.

It is also possible to use weakly anionic surfactants, such as the polyoxyalkylenated alkyl amide or alkyl ether carboxylic acids, such as those containing 2 to 50 ethylene oxide groups.

The nonionic surfactants are more particularly chosen from the polyethoxylated or polypropoxylated alcohols, α-diols, alkylphenols and fatty acids, with a fatty chain containing 8 to 18 carbon atoms, the number of ethylene oxide or propylene oxide groups being between 2 and 50 and the number of glycerol groups being between 2 and 30.

It is more particularly possible to mention the copolymers of ethylene oxide and of propylene oxide; the condensates of ethylene oxide and of propylene oxide with fatty alcohols; the polyethoxylated fatty amides having preferably 2 to 30 mol of ethylene oxide; the polyethoxylated fatty amines having preferably 2 to 30 mol of ethylene oxide; the oxyethylenated fatty acid esters of sorbitan having preferably 2 to 30 mol of ethylene oxide; the fatty acid esters of sugar, the fatty acid esters of polyethylene glycol, the fatty acid esters of glycols; the amine oxides such as the oxides of ($C_{10}$–$C_{14}$)-alkylamines or of N-acylamidopropylmorpholine.

The preferred amphoteric or zwitterionic surfactants are the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the ($C_8$–$C_{20}$) alkylbetaines, the sulfobetaines, the ($C_8$–$C_{20}$)alkylamido ($C_1$–$C_6$)alkylbetaines or the ($C_8$–$C_{20}$)alkylamido($C_1$–$C_6$) alkylsulfobetaines.

It is also possible to mention the alkylpeptides or the alkylimidazolium betaines.

Among the amine derivatives, there may be mentioned the products marketed under the name "Miranol", such as those described in U.S. Pat. Nos. 2,528,378 and 2,781,354 or listed in the CTFA dictionary, 3rd edition, 1982, under the names of Amphocarboxyglycinates or of Amphocarboxypropionates.

The cationic surfactants are chosen from the quaternary ammonium salts, such as the ($C_8$–$C_{22}$) alkyltrimethylammonium halides, the ($C_8$–$C_{22}$) dialkyldimethylammonium halides or the ($C_8$–$C_{22}$) alkyldimethylhydroxyethylammonium halides.

The additional cosurfactants can represent up to 50% of the total weight of the surfactants present in the composition.

The pH of the compositions in accordance with the invention is generally between 2 and 10.5 and more particularly between 3 and 8.

Insofar as the cosmetically acceptable medium of the composition according to the invention is an aqueous medium, it may consist solely of water or of a mixture of water and of a cosmetically acceptable solvent, such as $C_1$–$C_4$ lower alcohols, such as ethanol, isopropanol or n-butanol; alkylene glycols, such as propylene glycol: or glycol ethers.

The compositions according to the invention can be provided in the form of a more or less thickened liquid, a gel, an emulsion (milk or cream), an aqueous/alcoholic lotion, a dispersion, a solid bar or an aerosol foam.

The compositions are, for example, emollient lotions, milks or creams, lotions, milks or creams for caring for keratinous substances, make-up removal creams or milks, foundation bases, antisun lotions, milks or creams, lotions, milks or creams for artificial tanning, shaving creams or foams, aftershave lotions, face masks, make-up products for the eyes, nail varnishes, colors and foundations for the face, shampoos, bath or shower products, compositions to be rinsed or not to be rinsed, to be applied before or after shampooing, dyeing, bleaching, perming or hair straightening, or compositions for dyeing, bleaching, perming or straightening the hair.

The compositions in accordance with the invention can also contain, in addition, various additives such as thickening agents, such as polyacrylic acids, cellulose derivatives or esters of fatty acids and of polyethylene glycol; sequestering agents; foam reinforcers; preservatives; fragrances; electrolytes; fatty substances, such as fatty alcohols, ceramides or mineral, vegetable, animal or synthetic oils or waxes; UV screening agents; agents for combating free radicals; pearlescence agents; biocides; antibacterials; antidandruff agents; antiseborrheic agents; antiparasitic agents; repellents; dyes; pigments; oxidizing agents; reducing agents; moisturizers; anionic, nonionic or amphoteric polymers; vitamins or α-hydroxy acids.

Treatment of the keratinous substances is carried out by application to these substances of a cosmetically acceptable amount of a composition as defined above.

The process for washing and/or for conditioning the keratinous substances and in particular the hair or the skin in accordance with the invention consists in applying at least one composition as defined above to these substances, this application optionally being followed by a stage of rinsing with water.

The washing compositions can be used as shampoos but also as a shower gel for washing the hair and the skin, in which case they are applied to the wet skin and hair, which are rinsed after application.

When the compositions are used for conditioning the hair, they are applied to the wet hair, after which it may either be dried or, after an exposure time of 1 to 10 minutes, rinsed with water. It is observed that the wet hair disentangles readily.

The examples which follow are intended to illustrate the invention without having any limiting nature whatsoever.

EXAMPLE 1

A conditioning lotion (to be rinsed) with the following composition was prepared:

Sodium decyl D-galactoside uronate 1 g AM

Polytetramethylpropylenehexamethylenediammonium chloride, as a 60% solution 6 g AM Dyes, fragrance, preservative Water q.s. for 100 g pH adjusted to 5.5 with HCl

EXAMPLE 2

A foam bath with the following composition was prepared:

Sodium decyl D-galactoside uronate 30 g AM

Hydroxypropylated guar gum quaternized with 2,3-epoxypropyltrimethylammonium chloride, sold under the name of "Jaguar C 13S" by Meyhall 0.75 g Dyes, fragrance, preservative Water q.s. for 100 g pH adjusted to 7.5 with NaOH

EXAMPLE 3

A shampoo with the following composition was prepared:

Sodium decyl D-galactoside uronate 15 g

Sodium lauryl ether sulfate oxyethylated with 2 mol of ethylene oxide, sold as an aqueous solution containing 28% of active material (AM) 5 g AM Ether of myristyl glycol and of tallow oxyethylenated with 60 mol of ethylene oxide, sold under the name "Elfacos GT 282S" by Akzo 3 g Quaternium-76 Hydrolysed Collagen (INCI name, Ed. 93), sold under the name "Lexein QX 3000" by Inolex 1.5 g AM Fragrance, preservatives q.s.

Water q.s. for 100 g

EXAMPLE 4

A shampoo with the following composition was prepared:

Magnesium dodecyl D-galactoside uronate 10 g

Magnesium lauryl ether sulfate, sold under the name "Empicol BSD" by Albright & Wilson 3 g AM Polyquaternium-7 (INCI name, Ed. 93), sold under the name "Merquat 550" by Galgon 0.5 g AM Hydroxypropylated guar gum, sold under the name "Jaguar HP 60" by Meyhall 1 g Fragrance, preservatives q.s.

Water q.s. for 100 g

We claim:

1. Cosmetic composition, comprising, in a cosmetically acceptable aqueous medium:

(A) at least one alkylgalactoside uronate anionic surfactant of formula:

$$\text{(I)}$$

in which $R_1$ denotes a linear or branched alkyl radical containing 8 to 22 carbon atoms, R denotes a group (i) >CH—CH(OH)—$CO_2R_2$ or (ii) —CH(OH)—CH—$CO_2R_2$, in which the carbon carrying the hydroxyl group is connected to the endocyclic oxygen atom; $R_2$ being hydrogen, an alkali metal, an alkaline-earth metal or a quaternary ammonium group which is unsubstituted or substituted by alkyl or hydroxyalkyl radicals or an amino acid radical; and (B) at least one cationic polymer selected from the group consisting of noncellulose cationic polysaccharides and dimethyldiallylammonium chloride homopolymers and copolymers.

2. Composition according to claim 1, wherein, in the formula (I), the radical $R_2$ denotes sodium or potassium; magnesium; or the quaternary ammonium group derived from ammonia, triethanolamine, monoethanolamine, 2-amino-2-methyl-1,3-propanediol, 2-amino-2-methyl-1-propanol, histidine, arginine or lysine.

3. Composition according to claim 1, wherein $R_1$ denotes a $C_8$–$C_{14}$ alkyl.

4. Composition according to claim 1, wherein $R_1$ denotes a decyl radical.

5. Composition according to claim 4, wherein the compound of formula (I) is:

sodium decyl α-D-galactopyranoside uronate, sodium decyl β-D-galactopyranoside uronate, sodium decyl α-D-galactofuranoside uronate, or sodium decyl β-D-galactofuranoside uronate.

6. Composition according to claim 1, wherein the anionic surfactant of formula (I) is present in proportions of between 1 and 50% by weight and the cationic polymer is present in proportions of between 0.01 and 10% by weight; the percentages by weight being expressed with respect to the total weight of the composition.

7. Composition for conditioning keratinous substances according to claim 1, wherein the concentration of anionic surfactants of formula (I) is between 1 and 10% by weight with respect to the total weight of the composition.

8. Composition for washing keratinous substances according to claim 1, wherein concentration of anionic surfactants of formula (I) is between 4 and 50% by weight with respect to the total weight of the composition.

9. Composition according to claim 1, wherein the composition further contains an additional cosurfactant of anionic, nonionic, amphoteric or cationic type in a proportion ranging up to 50% of the total weight of surfactants.

10. Composition according to claim 9, wherein the additional anionic cosurfactant is chosen from fatty acids, alkyl sulfates, alkyl ether sulfates, alkylamidoether sulfates, alkylarylpolyether sulfates or monoglyceride sulfates; alkylsulfonates, alkylethersulfonates, alkylamidesulfonates, alkylarylsulfonates, olefinsulfonates or paraffinsulfonates; alkylsulfosuccinates, alkylethersulfosuccinates or alkylamidesulfosuccinates; alkylsulfosuccinamates; alkylsulfoacetates; alkyl ether phosphates; acylsarcosinates, acylglutamates or N-acyltaurates; or isethionates; alkyl or acyl radical consisting of a carbon chain containing from 10 to 20 carbon atoms or polyoxyalkylenated alkyl amide or alkyl ether carboxylic acids.

11. Composition according to claim 9, wherein the additional nonionic cosurfactant is chosen from polyethoxylated or polypropoxylated alcohols, α-diols, alkylphenols and fatty acids, with a fatty chain containing 8 to 18 carbon atoms, the number of ethylene oxide or propylene oxide groups being between 2 and 50 and the number of glycerol groups being between 2 and 30, the copolymers of ethylene oxide and of propylene oxide; the condensates of ethylene oxide and of propylene oxide with fatty alcohols; polyoxyethylenated fatty amides; polyoxyethylenated fatty amines; oxyethylenated fatty acid esters of sorbitan; fatty acid esters of sugar; fatty acid esters of polyethylene glycols; fatty acid esters of glycol; or amine oxides.

12. Composition according to claim 9, wherein the additional amphoteric cosurfactant is chosen from the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; $(C_8-C_{20})$alkylbetaines, sulfobetaines, $(C_8-C_{20})$alkylamido$(C_1-C_6)$alkylbetaines or $(C_8-C_{20})$alkylamido$(C_1-C_6)$alkylsulfobetaines; alkylpeptides; or alkylimidazolium betaines.

13. Composition according to claim 9, wherein the cationic cosurfactant is a quaternary ammonium salt.

14. Composition according to claim 1, wherein the cosmetically acceptable medium consists of water or a mixture of water and of a cosmetically acceptable solvent.

15. Composition according to claim 1, wherein the composition is in the form of a thickened liquid, a gel, an emulsion, an aqueous/alcoholic lotion, a dispersion, a solid bar or an aerosol foam.

16. Composition according to claim 1, wherein the composition further contains additives chosen from foam reinforcers, thickeners, sequestering agents, electrolytes, fragrances, preservatives, fatty alcohols, mineral, vegetable, animal or synthetic oils or waxes, ceramides, UV screening agents, agents for combating free radicals, pearlescence agents, biocides, antibacterials, antidandruff agents, antiseborrheic agents, antiparasitic agents, repellents, dyes, pigments, oxidizing agents, reducing agents, moisturizers, anionic, nonionic or amphoteric polymers, vitamins or α-hydroxy acids.

17. Process for cosmetic washing and/or conditioning of the hair or of the skin, comprising applying an effective amount for washing and/or conditioning the hair or the skin of the composition according to claim 1 to the skin or the hair, this application optionally being followed by a rinsing with water.

* * * * *